United States Patent [19]
Pierce

[11] Patent Number: 5,176,691
[45] Date of Patent: Jan. 5, 1993

[54] KNOT PUSHER

[75] Inventor: Javin Pierce, Winooski, Vt.

[73] Assignee: Pierce Instruments, Inc., Winooski, Vt.

[21] Appl. No.: 580,551

[22] Filed: Sep. 11, 1990

[51] Int. Cl.⁵ .............................................. A61B 17/00
[52] U.S. Cl. .................................... 606/148; 606/144
[58] Field of Search ....................... 606/139, 144–148; 289/1.5, 2, 17

[56] References Cited

U.S. PATENT DOCUMENTS

| 1,635,066 | 7/1927 | Wells | 606/145 |
| 2,610,631 | 9/1952 | Calicchio | 606/139 |
| 3,752,516 | 8/1973 | Mumma | 289/17 |
| 4,602,635 | 7/1986 | Mulhollan et al. | 606/144 |
| 4,641,652 | 2/1987 | Hutterer et al. | 606/148 |
| 4,961,741 | 10/1990 | Hayhurst | 606/139 |
| 5,087,263 | 2/1992 | Li | 606/144 |

FOREIGN PATENT DOCUMENTS

| 0305885 | 6/1971 | U.S.S.R. | 606/139 |
| 0649416 | 2/1979 | U.S.S.R. | 606/139 |

Primary Examiner—Stephen C. Pellegrino
Assistant Examiner—Gary Jackson
Attorney, Agent, or Firm—Thomas N. Neiman

[57] ABSTRACT

A device is provided for advancing a winding of a knot through a space which is too small for conventional methods. The device can be used, for example, to advance the knot of a suture through an endoscopic portal. The device has opposed pulley-like surface for guiding the ends of the suture away from the winding as the winding is advanced through the portal.

1 Claim, 6 Drawing Sheets

KNOT PUSHER

BACKGROUND OF THE INVENTION

1. Field of the Invention

The present invention relates to a device for pushing a winding of a knot through a space which is too small for conventional methods. More specifically, the present invention relates to a ligator for pushing a winding of a suture knot through an endoscopic portal.

2. Description of the Related Art

Several tools have been developed for tying knots at the distal end of an arthroscopic cannula. One such device consists of a ring at the end of a manipulatable rod. A suture winding is pushed by a distal end of the ring while one suture end passes through the ring. This type of knot pusher is unsatisfactory because it has no means for controlling the position of the winding. The winding may slip off the ring if tension is not accurately applied to the suture ends. Moreover, the winding tends to become locked into the ring. Moreover, the device and the winding do not form a streamlined system, resulting in frictional problems during use. For all of these reasons, the device is difficult to operate.

U.S. Pat. No. 4,602,635 to Mulhollan discloses a method of using a ligator to tie a knot through torn tissue. U.S. Pat. No. 2,610,631 to Calicchio discloses a ligator for tying a ligature loop around a blood vessel.

Other art of interest includes U.S. Pat. No. 4,641,652 to Hutterer, U.S. Pat. No. 3,752,516 to Mumma and U.S. Pat. No. 1,635,066 to Wells.

SUMMARY OF THE INVENTION

The present invention relates to a knot pusher formed of an elongated rod, the distal end of the rod including: (a) a face for pushing a suture winding through a small space, and (b) a pair of opposed guiding and retaining means for guiding the ends of a suture away from the winding and for retaining the winding against the face, the face including a depression for receiving the winding as the winding is pushed through the small space.

The present invention also relates to a method of tying a filament with an elongated rod which includes a distal end, the distal end including a pair of opposed pulley-like surfaces and a face, the face including a depression, the method consisting of the following steps: forming a first winding of the filament; locating the ends of the filament within the opposed eyelets; positioning the winding against the face such that the winding is received within the depression; and advancing the rod and thereby pushing the winding through a small space and, at the same time, pulling on the ends of the filament so as to advance the winding.

The present invention also relates to a knot pusher having an elongated body, the outer side surface of the elongated body including a face with a depression for receiving a winding, the face being generally parallel to the axis of the elongated body, the body including a pair of opposed eyelets for guiding the ends of sutures away from the winding and for retaining the winding against the face, the eyelets being generally transverse to the longitudinal axis of the elongated body.

The present invention also relates to a knot pusher formed of an elongated rod and a cylinder which surrounds the elongated rod, the rod including a face for pushing a suture winding through a small space, the cylinder including a pair of opposed pulley-like surfaces for guiding the ends of a suture away from the winding, the cylinder being slidable with respect to the rod so as to prevent the winding from binding.

The present invention also relates to a knot pusher formed of an elongated body, the outer surface of the rod having a pair of opposed pulley-like surfaces at the distal end of the rod for guiding the ends of a suture away from a winding, the pulley-like surfaces being axially reciprocatable with respect to each other.

The present invention also relates to a knot pusher formed of an elongated rod, the outer surface of the rod being provided, at the distal end of the rod, with a face for pushing a suture winding through a small space and a pair of opposed eyelets for guiding the ends of a suture away from the winding and for retaining the winding against the face, the knot pusher also having closure bars for selectively opening and closing the eyelets.

The present invention also relates to a knot pusher formed of an elongated rod, the outer surface of the rod being provided, at the distal end of the rod, with a face for pushing a suture winding through a small space and a pair of opposed pulley-like surfaces for guiding suture ends away from the winding and for retaining the winding against the face, the knot pusher also having a cutting tube for cutting the suture ends.

The present invention also relates to a knot pusher formed of two elongated members, each of which has a pulley-like surface for guiding a suture end, the pulley-like surfaces being located at the distal ends of the elongated members, the elongated members being individually manipulatable so as to advance a suture winding through a small space.

The present invention also relates to a method of tying a knot, consisting of the following steps: forming a first winding of filament; locating the ends of the filament against opposed pulley-like surfaces; using the pulley-like surfaces to advance the first winding through a small space; thereafter retracting the pulley-like surfaces; after retracting the pulley-like surfaces, forming a second winding of the filament; and using the pulley-like surfaces to advance the second winding through the small space toward the first winding to complete the knot.

Other features and advantages of the present invention will become apparent from the following description of preferred embodiments of the invention with reference to the accompanying drawings

DETAILED DESCRIPTION OF THE PREFERRED EMBODIMENTS

Figure 1:
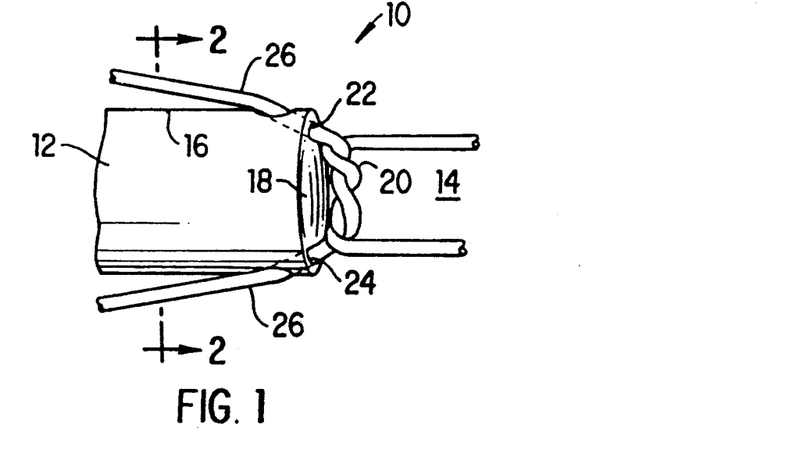
FIG. 1 is a partial, perspective view of a knot pusher in accordance with the present invention.

Referring now to the drawings, wherein like reference numerals indicate like elements, there is shown in FIG. 1 a knot pusher which is constructed in accordance with the principles of the present invention and which is designated generally by reference numeral 10.

The knot pusher 10 generally has the shape of an elongated rod 12. The rod 12 has a distal end 14, a cylindrical outer surface 16 and a proximal end (not shown). The distal end 14 has a face 18 for pushing on a suture winding 20 and opposed eyelets 22, for guiding and retaining suture ends 26.

Figure 2:
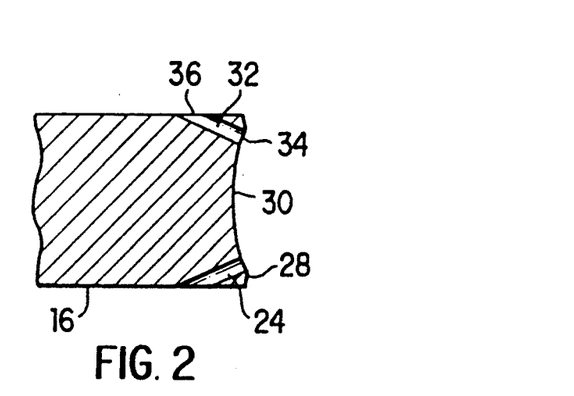
FIG. 2 is a partial, cross sectional view through the line 2—2 of FIG. 1.

The face 18 has a circular periphery 28 (FIG. 2) and a space or concave, smoothly dished out cup or depression 30. The depression 30 is located radially within the periphery 28. Preferably, the periphery 28 lies within a plane which is perpendicular to the cylindrical surface 16, with the outer diameter of the circular periphery 28 being equal to the diameter of the cylindrical surface 16.

The eyelet 22 includes a generally cylindrical passageway 32 with an inlet 34 and an outlet 36. The inlet 34 is located in the face 18, near the periphery 28. The inlet 34 is preferably about 1.5 times as wide as the suture ends 26, such that one suture end can pass freely therethrough and such that two suture ends will not jam therewithin. The outlet 36 is located on the cylindrical outer surface 16 of the rod 12. The passageway 32, inlet 34 and outlet 36 form a pulley-like surface for guiding one of the suture ends 26. Preferably, the pulley-like surfaces are formed of polished steel.

The eyelet 24 is identical to the eyelet 22. The opposed eyelets 22, 24 are symmetrical with respect to the axis of the rod 12.

In operation, a suture is stitched through tissue near a distal end of an arthroscopic portal, such as a cannula (not shown). The suture ends 26 are then brought out of the cannula and a first winding 20 of a double square knot type ligature is formed. Tension is then applied to the suture ends 26 and, at the same time, the rod 12 is moved forward, causing the face 18 to push the winding 20 in the distal direction toward the tissue. As the rod 12 is advanced, the suture passes through the eyelets 22, 24 in the proximal direction, narrowing the distance between the winding 20 and the stitched tissue until the winding 20 is tightened. To prevent binding, or to unjam the winding 20, tension may be applied alternately to the suture ends 26 in a reciprocating fashion, i.e. with a see-sawing or jiggling motion. Ideally, the suture does not move within the stitched tissue during the tightening of the winding 20.

During this process, the eyelets 22, 24 direct the suture ends 26 from opposite sides of the winding 20 toward the proximal end of the elongated rod 12. Since the eyelets 22, 24 are spaced apart from each other on opposite sides of the face 18, the eyelets 22, 24 also cooperate to prevent the winding 20 from sliding off the face 18 during ligation. The depression 30 also assists in maintaining the winding in place on the face 18.

The knot pusher 10 and the winding 20 cooperate to form a streamlined, easy-to-control system. No part of the pusher 10 extends radially outward beyond the cylindrical outer surface 16. By maintaining the winding 20 within the depression 30, the winding 20 will not jam between the outer surface 16 and the walls of the cannula. The streamlined nature of the system makes it easy to push the winding 20 smoothly through the narrow cannula.

After the winding 20 is tightened, the distal end 14 of the knot pusher 10 may be retracted or removed, leaving the winding 20 tightly in place. The operation may then be repeated to apply a second winding over the first, to form a complete knot, such as a surgeon's knot or double square knot. Other types of knots may be formed by the present invention.

To push the rod 12 into the cannula, the proximal end of the rod 12 may be manipulated by an assistant. Alternatively, the suture ends 26 can be wrapped onto two fingers of one of the surgeon's hands, the other hand being free to advance the rod 12. Alternatively, the proximal end of the rod 12 may be clipped to and/or manipulated by the surgeon's body. In the latter case, the proximal end of the rod 12 is large enough such that the rod 12 can be advanced by the surgeon's abdomen without pain.

All of the edges of the knot pusher 10 are flared or chamfered to prevent damage to suture or tissue and to allow the system to pass easily through the small cannula.

Figure 3:
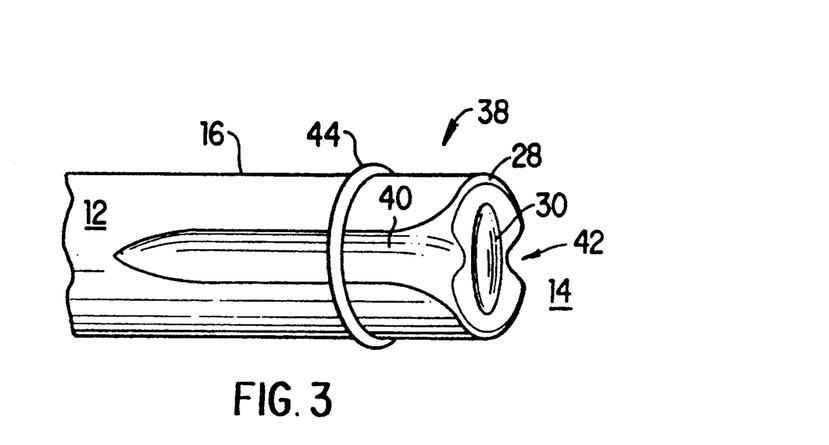
FIG. 3 is a partial, perspective view of another knot pusher in accordance with the present invention.

FIG. 3 illustrates a knot pusher 38 with eyelets which are formed by opposed, symmetrical diverging grooves 40, 42 and a ring 44. The grooves 40, 42 form pulley-like surfaces for guiding suture ends 26. The knot pusher 38 is otherwise identical to the knot pusher 10. In operation, the suture ends 26 pass relatively through the grooves 40, 42 as the rod 12 moves in the distal direction toward the stitched tissue. The ring 44 prevents the suture from falling out of the grooves 40, 42. The winding 20 is thus prevented from falling off the face 18. The depression 30 assists in maintaining the winding 20 in place on the face 18.

Figure 4:
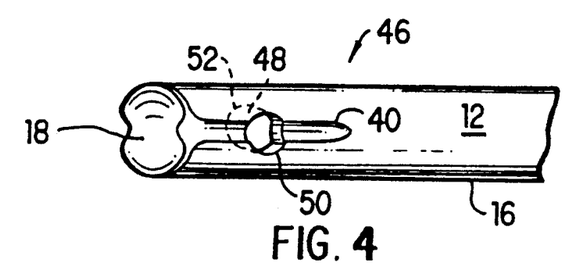
FIG. 4 is a partial, perspective view of another knot pusher in accordance with the invention.

FIG. 4 illustrates a knot pusher 46 with eyelets which are formed by opposed, symmetrically diverging grooves (only one of which can be seen at 40) and a transversely extending hole 48. The hole 48 has two ends 50, 52 which are located within the diverging grooves 40, 42. In operation, suture ends 26 are guided through the diverging grooves 40, 42 and pass in opposite directions through the transverse hole 48. Thus, the transverse hole 48 prevents the suture ends 26 from falling out of the diverging grooves 40, 42. Unlike the knot pusher 38 illustrated in FIG. 3, the knot pusher 46 does not have a ring 44. The knot pusher 46 is otherwise identical to the knot pusher 38.

Figure 5:
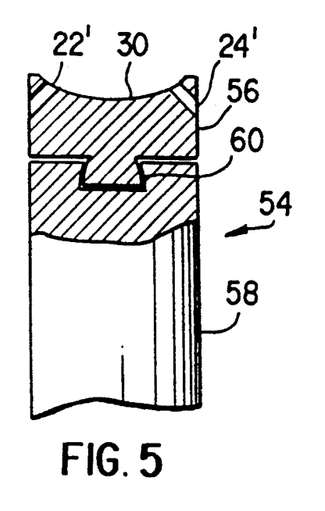
FIG. 5 is a partial, cross sectional side view of another knot pusher in accordance with the invention.

FIG. 5 shows a knot pusher 54 which has a distal end 56 which is removable from a main body 58. The distal end 56 may be formed of Teflon and is disposable. The main body 58 is reusable. The distal end 56 and main body 58 are connected to each other by a dovetailed interface indicated generally at 60. The knot pusher 54 is otherwise identical to the knot pusher 10 illustrated in FIG. 1.

Figure 6:
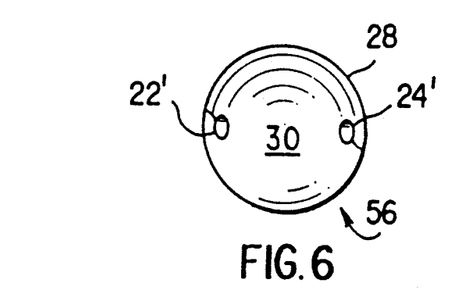
FIGS. 6 and 7 are top and side views, respectively, of a distal end of the knot pusher of FIG. 5.
Figure 7:
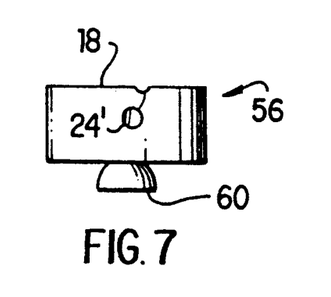

As illustrated in FIGS. 6 and 7, the eyelets 22', 24' of the distal end 56 include means for permitting suture ends 26 to be snapped directly therein. With the arrangement illustrated in FIGS. 6 and 7, the suture ends 26 do not have to be threaded through the eyelets 22', 24'.

Figure 8:
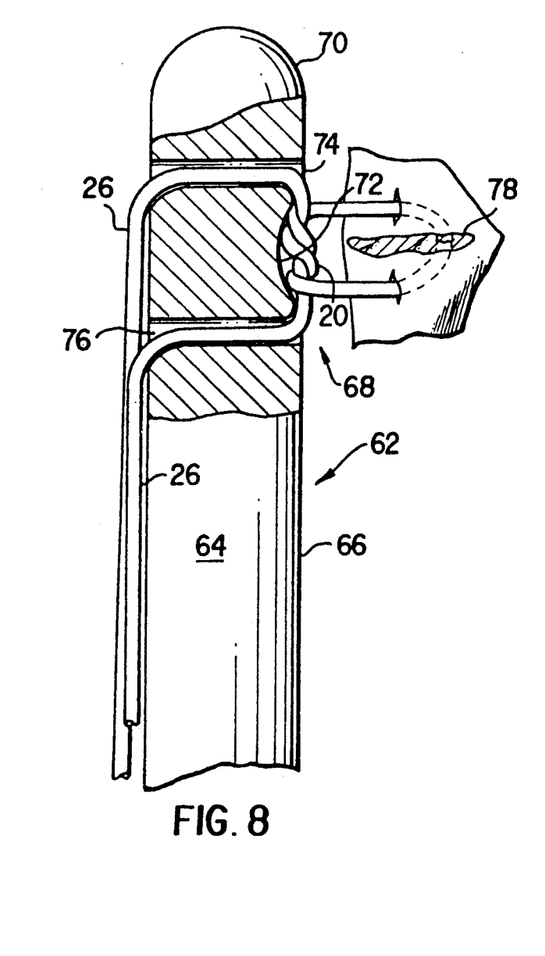
FIG. 8 is a partial, cross sectional side view of another knot pusher in accordance with the invention.

FIG. 8 illustrates a knot pusher 62 which is designed to be used like a catheter for side delivery of a winding 20. The knot pusher 62 includes an elongated body 64 with an outer surface 66. The outer surface 66 has a face 68 which is located near the distal end 70 of the knot pusher 62. The face 68 includes a depression 72 which is like the depression 18 illustrated in FIG. 1. The knot pusher 62 further includes eyelets 74, 76 for guiding suture ends 26 away from the winding 20. The eyelets 74, 76 extend transversely through the body 64.

In operation, the winding 20 is positioned within the depression 72 and the distal end 70 is advanced toward a lesion 78 to be stitched. Tension is applied to the suture ends 26 as the face 68 is advanced toward the lesion 78. This has the effect of pushing the winding 20 toward the lesion 78, slack suture between the winding 20 and the lesion 78 being taken up until the winding 20 forms a tightened first pass of a knot at the lesion 78. The knot pusher 62 is then retracted or pulled away from the lesion 78, and the suture ends 26 are allowed to slide in an opposite direction through the eyelets 74, 76. The process is then repeated with a second winding to form a knot.

Figure 9:
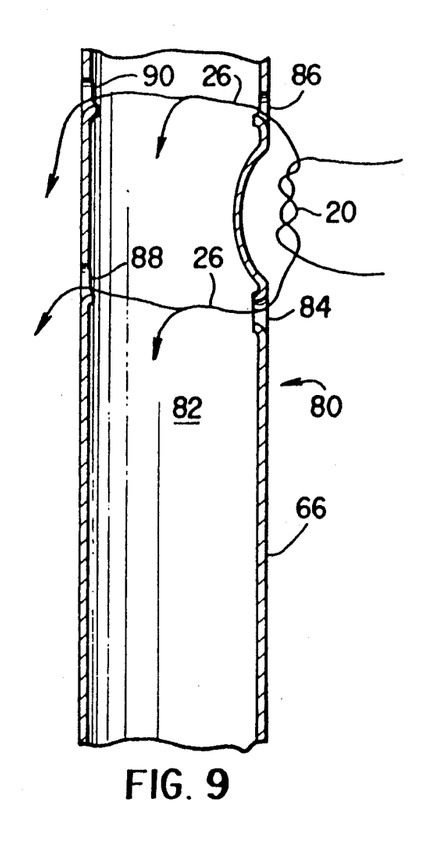
FIG. 9 is a partial, cross sectional side view of another knot pusher in accordance with the invention.

FIG. 9 illustrates a knot pusher 80 which, like the knot pusher 62 illustrated in FIG. 8, is adapted to push a winding 20 in a sideways direction. The knot pusher 80 has a hollow interior 82. Thus, eyelets are formed by four openings 84, 86, 88 and 90. Suture ends 26 may pass through all four of the openings 84-90 and then axially outside of the pusher 62, or through only the openings 84 and 86 and then axially toward the proximal end of the knot pusher 80 through the hollow interior 82. The knot pusher 80 is otherwise identical to the knot pusher 62 illustrated in FIG. 8.

Figure 10:
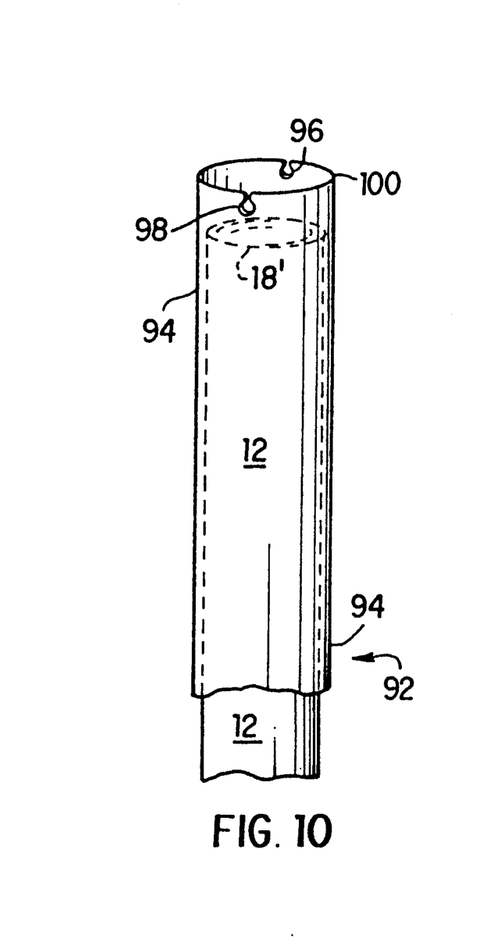
FIG. 10 is a broken away perspective view of another knot pusher in accordance with the invention.

FIG. 10 illustrates a knot pusher 92 which includes an elongated rod 12 and an outer cylinder 94. The elongated rod 12 includes a face 18' which is identical to the face 18 illustrated in FIG. 1 except that the face 18' has no eyelets. Eyelets 96, 98 with pulley-like surfaces are formed through a distal end 100 of the cylinder 94. The operation of the knot pusher 92 is similar to the operation of the knot pusher 10 illustrated in FIG. 1, with a winding 20 being received against the face 18' and with suture ends 26 passing through and being guided by the pulley-like surfaces. An important difference is that the cylinder 94 can be moved axially with respect to the rod 12 so as to help keep the winding 20 from binding as it is advanced in the distal direction. The cylinder 94 and the rod 12 can be manipulated by the surgeon outside of the arthroscopic portal.

Figures 11, 12:
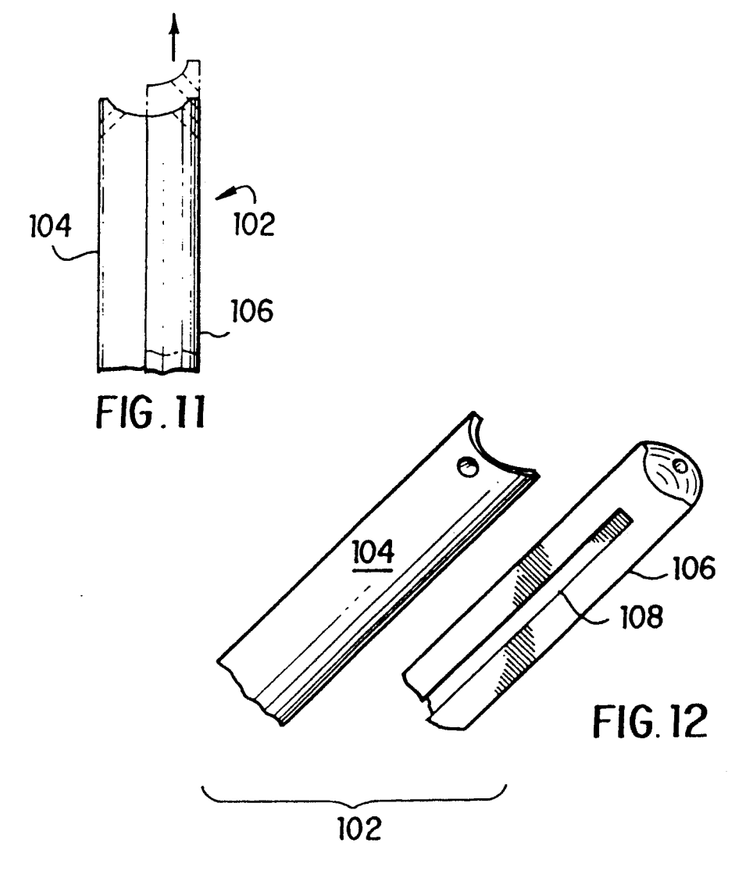
FIG. 11 is a schematic, cross sectional view of another knot pusher in accordance with the invention.
FIG. 12 is a detailed, exploded perspective view of the knot pusher of FIG. 11.

FIG. 11 illustrates a knot pusher 102 which is identical to the knot pusher 10 illustrated in FIG. 1, except that the knot pusher 102 is formed of two elongated parts 104, 106. The parts 104, 106, when aligned with respect to each other as illustrated in solid lines in FIG. 11, operate the same as the knot pusher 10 of FIG. 1. But the parts 104, 106 can be moved axially with respect to each other, as illustrated in dotted lines in FIG. 11 by manipulation of the proximal end of the pusher 102 between the surgeon's thumb and forefinger. This way, both proximal ends of the suture ends 26 can be held at one point. That is, the suture ends 26 do not have to be reciprocated to prevent the winding 20 from binding as it is advanced in the distal direction. The features illustrated in FIG. 11 can also be used to change the angular position of the winding 20 just prior to tightening.

The knot pusher 102 has a solid body. As illustrated in detail of FIG. 12, the parts 104 and 106 of the knot pusher 102 are held together in slidable relationship by a dovetail connection 108. A tubular (i.e., hollow) knot pusher can also be formed to have the axially reciprocating feature illustrated in FIG. 11.

Figure 13:
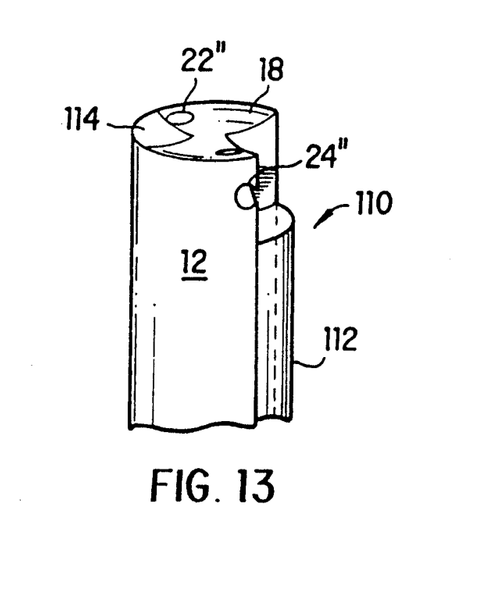
FIG. 13 is a partial, perspective view of another knot pusher in accordance with the invention.

FIG. 13 illustrates a knot pusher 110 which is identical to the knot pusher 10 illustrated in FIG. 1 except that the knot pusher 110 has elongated wedge-shaped eyelet closure bars 112, 114 which can be used to open and close eyelets 22", 24". To position suture ends 26 within the eyelets 22", 24", the distal ends of the eyelet closure bars 112, 114 are moved away from the eyelets 22", 24" in either an axial, proximal direction or a radially outward direction. This opens the sides of the eyelets 22", 24", i.e., exposes the passageways. After the suture ends 26 have been positioned within the eyelets 22", 24", the bars 112, 114 are repositioned. When the knot pusher 110 is arranged as illustrated in FIG. 13, the eyelet 22" is closed by the bar 114 and the eyelet 24" is open.

Figure 14:
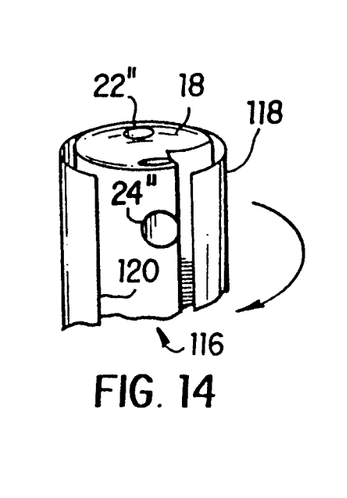
FIG. 14 is a schematic view of another knot pusher in accordance with the invention.

FIG. 14 illustrates a knot pusher 116, the operation of which is similar to the operation of the knot pusher 110 illustrated in FIG. 13. The knot pusher 116 has a sleeve 118 with a slit 120. The sleeve 118 can be rotated around the eyelets 22", 24" to selectively open and close the eyelets 22", 24".

Figure 15:
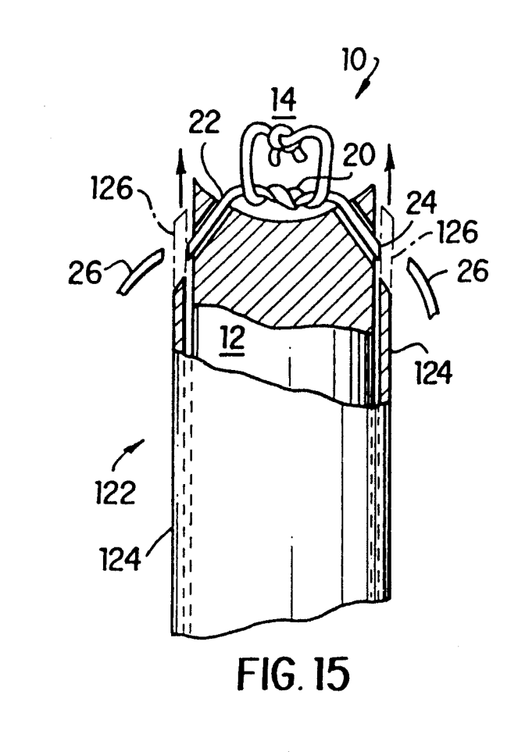
FIG. 15 is a partial, broken away, cross sectional side view of another knot pusher in accordance with the invention.

FIG. 15 illustrates a system 122 which includes the knot pusher 10 illustrated in FIG. 1 and which further includes a cutting tube 124. The cutting tube 124 is slidable toward the distal end 14 of the knot pusher 10. The tube 124 has a sharpened distal end 126 which cuts suture ends 26 after a knot has been formed. The cutting tube 124 can also be used with the knot pushers 62 and 80 illustrated in FIGS. 8 and 9.

Figure 16:
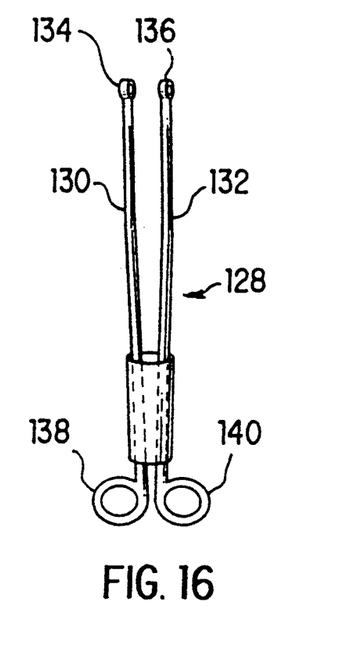
FIG. 16 is a side view of another knot pusher in accordance with the invention.

FIG. 16 illustrates a knot pusher 128 which is formed of two elongated members 130, 132. Each elongated member 130, 132 includes an eyelet 134, 136 at a distal end thereof and finger receiving holes 138, 140 at a proximal end thereof.

Figure 17:
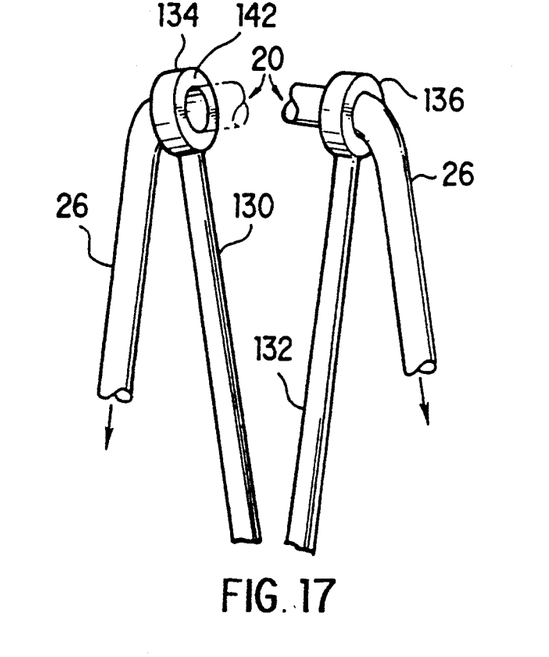
FIG. 17 is a detailed view of the distal end of the knot pusher of FIG. 16.
Figure 18:
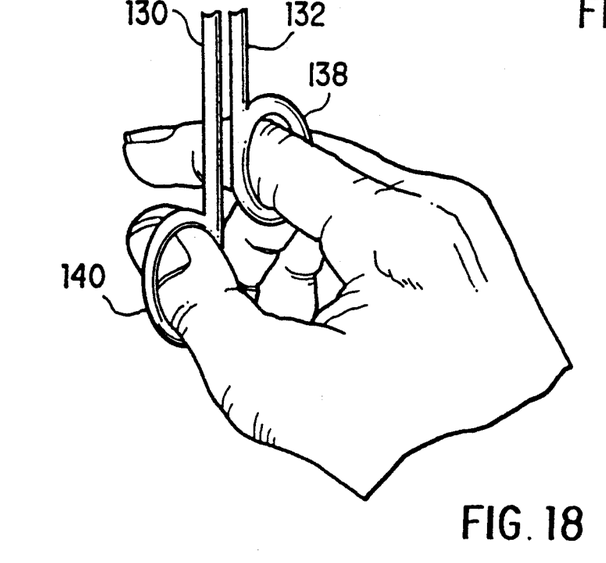
FIG. 18 is a detailed view of the proximal end of the knot pusher of FIG. 16.

The eyelets 134, 136 can be moved forward and away from each other. As illustrated in detail in FIG. 17, the eyelets 134, 136 can be spaced wide enough apart so that a winding 20 contacts only one of the eyelets 134, 136 at a time. The inner sides of the eyelets 134, 136 have annular, fender or contact surfaces, only one of which can be seen at 142. In operation, the winding 20 is maintained between the surfaces 142 while tension is applied to the suture ends 26. The suture ends 26 can be pulled with a reciprocating action. Alternatively, the members 130, 132 themselves can be axially reciprocated with respect to each other by appropriate manipulation of the receiving holes 138, 140, as illustrated in FIG. 18.

As in all of the embodiments disclosed herein, the knot pusher 128 has pulley-like surfaces for guiding suture ends 26 away from a winding 20 and for maintaining the winding 20 in place with respect to the knot pusher 128 as the knot pusher 128 is advanced into an arthroscopic portal.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A knot pusher, comprising an elongated rod with a distal end and an outer surface, the distal end including: (a) a face for pushing a suture winding through a small space, and (b) a pair of opposed guiding and retaining means for guiding suture ends away from the winding and for retaining the winding against the face, the face including a depression for receiving the winding as the winding is pushed through the small space.

* * * * *